(12) United States Patent
Reich et al.

(10) Patent No.: US 6,287,546 B1
(45) Date of Patent: *Sep. 11, 2001

(54) SHAMPOOS WITH STABILIZERS

(75) Inventors: Charles Reich, Highland Park; Janine Chupa; Cheryl L. Kozubal, both of Somerset; Dean Terng-Tzong Su, Princeton Junction, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/406,543

(22) Filed: Sep. 27, 1999

Related U.S. Application Data

(60) Provisional application No. 60/103,830, filed on Oct. 9, 1998.

(51) Int. Cl.⁷ ............................. A61K 7/06; A61K 7/075
(52) U.S. Cl. .................. 424/70.121; 424/70.11; 424/70.12; 424/70.19; 424/70.21; 424/70.22; 424/70.24
(58) Field of Search ............................. 424/70.121, 70.11, 424/70.12, 70.19, 70.22, 70.24

(56) References Cited

U.S. PATENT DOCUMENTS

| | | |
|---|---|---|
| 2,528,378 | 10/1950 | Mannheimer et al. . |
| 3,907,984 | 9/1975 | Calvert et al. . |
| 4,012,501 | 3/1977 | Farber . |
| 4,223,009 | 9/1980 | Chakrabarti . |
| 4,728,457 | 3/1988 | Fieler et al. . |
| 4,741,855 | 5/1988 | Grote et al. . |
| 4,774,310 | 9/1988 | Butler . |
| 4,902,499 | 2/1990 | Bolish, Jr. et al. . |
| 4,963,348 | 10/1990 | Bolich, Jr. et al. . |
| 5,015,415 | 5/1991 | Goze et al. . |
| 5,075,103 | * 12/1991 | Halloran et al. . |
| 5,684,112 | 11/1997 | Berthiaume et al. . |
| 5,714,446 | 2/1998 | Bartz et al. . |
| 5,817,302 | 10/1998 | Berthiaume et al. . |

FOREIGN PATENT DOCUMENTS

| | | |
|---|---|---|
| WO 9217154 | 4/1991 | (EP) . |
| 0463780 | 1/1992 | (EP) . |
| WO 9210161 | 11/1991 | (WO) . |
| WO 9408557 | 4/1994 | (WO) . |

* cited by examiner

Primary Examiner—Thurman K. Page
Assistant Examiner—P. E. McQueeney
(74) Attorney, Agent, or Firm—Rosemary M. Miano

(57) ABSTRACT

This invention relates to improved stabilized shampoo compositions containing siloxysilicate materials commonly referred to as MQ resins, wherein the stabilizers are selected from (i) long chain fatty alcohols with greater than 14 carbons; (ii) acrylates/steareth-20 methacrylate copolymer; acrylates copolymer; and acrylates/C10–30 alkyl acrylate crosspolymer; and (iii) selected N,N-disubstituted phthalamic acids and their ammonium salts.

22 Claims, No Drawings

SHAMPOOS WITH STABILIZERS

This Application claims benefit of Prov. No. 60/103,830 filed Oct. 9, 1998.

FIELD OF THE INVENTION

This invention relates to improved stabilized shampoo compositions containing siloxysilicate materials commonly referred to as MQ resins. This case is related to a copending case, U.S. Ser. No. 09/169,656 filed Oct. 9, 1998, and owned by the same company.

BACKGROUND OF THE INVENTION

Human hair becomes soiled from exposure to environmental factors as well as from the sebum secreted by the scalp. The build-up of the sebum causes the hair to have a dirty and/or greasy feel and an unattractive appearance. It is the function of shampoo products to cleanse the hair and scalp by removing the excess dirt and sebum. However, it is also desired to cleanse the hair and scalp in such a way that the hair is left in an undamaged and manageable conditions. A number of approaches to formulating improved shampoos have included the creation of 2-in-1 products with conditioners (such as linear silicones) built into the shampoos. Rinse products may also be used as separate conditioning treatments and sprays can be used as detanglers.

A number of examples of conditioning shampoos and/or hair care products can be seen in U.S. Pat. No. 4,741,855 which describes shampoo compositions comprising 5–70% of a synthetic surfactant, 0.01–10.0% of an insoluble, non-volatile silicone, 0.5–5.0% of selected long chain derivatives and water.

Other background information may be found in U.S. Pat. Nos. 5,714,446; 3,907,984; 4,774,310; 4,223,009; 4,012,501; 5,684,112; and 4,728,457; and PCT case WO 92/17154.

There still remains a need for improved shampoo compositions, especially those which give benefits such as improved feel, manageability, shine and styling improvements (for example increased volume) to the hair. Thus it is an object to provide such shampoo compositions, particularly with the added benefit of being able to retain stability for the additives and at the same time delivering sufficient material to impart a beneficial effect. It is another object of the invention to provide shampoo compositions which contain MQ resins and to retain the stability of the compositions. It is yet another object of the invention to provide stable shampoo compositions which can be formulated with a variety of MQ resins depending on the types of properties desired, for example, increased shine, conditioning effects, reduced combing force, curl retention, volume and/or better manageability. These and other objects of the invention will become apparent from the following description.

SUMMARY OF THE INVENTION

The invention provides a detersive shampoo for cleansing the hair and providing improved feel, manageability, shine and styling improvements (for example increased volume) to the hair. The shampoo comprises:
 (a) a detersive surfactant;
 (b) a siloxysilicate resin (also called an MQ resin);
 (c) a stabilizer for the siloxysilicate; and
 (d) an aqueous carrier.

DETAILED DESCRIPTION OF THE INVENTION

The invention comprises stabilized shampoo formulations comprising:
 (a) from 4–60% of a detersive surfactant (for example, 5–50% and, more particularly, 5–30%);
 (b) from 0.1–15% of at least one siloxysilicate material (for example, 0.1–10% and, more particularly, 0.1–7.0%);
 (c) from 0.10–7.00% of a selected stabilizing agent (for example, 0.1–5% and, more particularly, 1.5–3%); and
 (d) the remainder being an aqueous carrier (optionally with other ingredients). Optionally other ingredients especially fragrance and/or preservative(s) may be included.

The surfactant can be selected from a variety of materials. Suitable surfactants include:
 (a) anionics as described in U.S. Pat. No. 4,902,499 to Bolich et al and U.S. Pat. No. 4,963,348 to Bolich et al both of which are incorporated by reference herein such as
  (i) alkyl and alkyl ether sulfates of formula $R^{20}OSO_3M$ and $R^{20}O(C_2H_4O)_wSO_3M$, wherein $R^{20}$ is alkyl or alkenyl of 10–20 carbon atoms, w is a number from 1 to 10, and M is a water-soluble cation such as ammonium, sodium, potassium and triethanolamine;
  (ii) reaction products of fatty acids (for example, those derived from coconut oil) esterified with isethionic acid and neutralized with sodium hydroxide;
  (iii) succinamates (for example disodium N-octadecylsulfosuccinates, tetrasodium N-(1,2-dicarboxyethyl)-N-octadecylsulfosuccinamate, diamyl ester of sodium sulfosuccicinic acid, dihexyl ester of sodium sulfosuccinic acid, and dioctyl esters of sodium sulfosuccinic acid; and
  (iv) olefin sulfonates having 12 to 24 carbon atoms;
 (b) amphoterics as described in U.S. Pat. No. 4,902,499 to Bolich et al and incorporated by reference herein such as:
  (i) derivatives of aliphatic secondary and tertiary amines in which the aliphatic radical can be straight chain or branched and wherein one of the aliphatic substituents contains from 8 to 18 carbon atoms and one contains an anionic water solubilizing group (for example, carboxy, sulfonate, sulfate, phosphate, or phosphonate) with examples of such compounds including sodium 3-dodecyl-aminopropionate, sodium 3-dodecylaminopropane sulfonate, N-alkyltaurines, N-higher alkyl aspartic acids (for example a products sold under the name "MIRANOL" as described in U.S. Pat. No. 2,528,378);
  (ii) zwitterionic surfactants (broadly exemplified as derivatives of aliphatic quaternary ammonium, phosphonium, and sulfonium compounds, in which the aliphatic radicals can be straight chain or branched, and wherein one of the aliphatic substitutents contains from 8 to 18 carbon atoms and one contains an anionic water-solubilizing group (for example, carboxy, sulfonate, sulfate, phosphate, or phosphonate);
  (iii) betaines, for example, high alkyl betaines such as cocodimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxymethyl betaine, stearyl bis-(2-hydroxy-propyl)

carboxymethyl betaine, oleyl dimethyl-gamma-carboxypropyl betaine, lauryl bis-(2-hydroxypropyl) alpha-carboxyethyl betaine, and cocamidopropyl betaine.

(c) nonionic surfactants including those selected from the group described in U.S. Pat. No. 4,741,855 to Grote et al and incorporated by reference herein; these are (i) polyethylene oxide condensates of alkyl phenols wherein the alkyl portion of the alkyl phenol has 6–12 carbons and may be straight chain or branched and the ethylene oxide portion is present in an amount of 10–60 moles of ethylene oxide per mole of alkyl phenol;

(ii) condensation products of ethylene oxide with a product resulting from the reaction of propylene oxide and ethylene diamine varied according to the hydrophobic/hydrophilic balance desired (for example, compounds containing from 40–80% polyoxyethylene by weight and having a molecular weight of from 5,000–11,000 resulting from the reaction of ethylene oxide groups with a hydrophobic base constituted of the reaction product of ethylene diamine and excess propylene oxide, wherein the base has a molecular weight of 2500–3,000);

(iii) condensation products of C8–18 straight or branched chain aliphatic alcohols with ethylene oxide (for example, coconut alcohol ethylene oxide condensate with 10–30 moles of ethylene oxide per mole of coconut alcohol wherein the coconut fraction has 10–14 carbon atoms);

(iv) long chain tertiary amine oxides of formula $(R^{30})(R^{31})(R^{32})$—N→O, wherein $R^{30}$ is an C8–18 alkyl, alkenyl or monohydroxy alkyls; which has from 0–10 ethylene moieties and from 0–1 glyceryl moiety; and $R^{31}$ and $R^{32}$ may be the same or different and are each independently selected from the group consisting of C1–3 alkyls with 0–1 hydroxy group. The arrow in the structure is a conventional representation of a semi-polar bond. Examples of suitable long chain tertiary amine oxides include cocamidopropylamine oxide and lauramine oxide;

(v) long chain tertiary phosphine oxides of Formula: $R^{20}R^{21}R^{22}P \rightarrow O$ where $R^{20}$ contains a C8–18 alkyl, alkenyl or monohydroxyalkyl radical; 0–10 ethylene oxide moieties and 0–1 glyceryl moiety; and $R^{21}$ and $R^{22}$ are each independently C1–3 alkyl or monohydroxyalkyl. (The arrow in the formula is a conventional representation of a semi-polar bond.); and (vi) long chain dialkyl sulfoxides containing one short chain alkyl or hydroxy alkyl radical of 1–3 carbons (particularly methyl) and one long hydrophobic chain having a C8–20 alkyl, alkenyl, hydroxy alkyl or keto alkyl group, with 0–10 ethylene oxide moieties and 0–1 glyceryl moiety.

Examples of particular surfactants include 5–50% of an anionic surfactant; 5–30% of a mixed anionic and amphoteric surfactant system where the ratio of anionic to amphoteric is from 60:40–40:60.

Particular examples of surfactants include: ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauroyl sulfate, triethanolamine lauroyl sulfate, triethanolamine lauroyl sulfate, monoethanolamine cocoyl sulfate, monoethanolamine lauroyl sulfate, sodium tridecyl benzene sulfonate and sodium dodecyl benzene sulfonate and others described in U.S. Pat. No. 4,902,499 to Bolich et al at Columns 4–6 incorporated by reference herein.

The siloxysilicates useful in this invention may be represented by Formula IA:

Formula IA

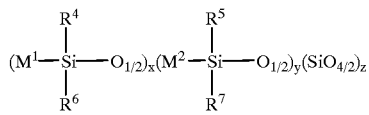

wherein $R^4$, $R^5$, $R^6$, and $R^7$ are each independently selected from the group consisting of phenyl and C1–C12 branched and unbranched hydrocarbons, particularly C1–C12 branched and imbranched alky, more particularly branched and unbranched C1–C5 alkyl and especially methyl;

$M^1$ and $M^2$ are each independently from the group consisting of
(a) hydrogen,
(b) phenyl,
(c) phenethyl,
(d) a polyether of Formula II:

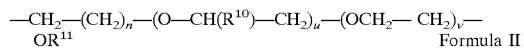

Formula II where n is a number from 1–20 and the —$(CH_2)$— chain may optionally contain 1 or 2 unsaturations; u and v are integers each independently selected from 0–20, provided that u+v≧1; $R^{10}$ is selected from C1–C20 alkyl; and $R^{11}$ is selected from the group consisting of H, —$CH_3$ and —$C(O)CH_3$); and (e) C1–C24 branched and unbranched hydrocarbons optionally substituted by a halogen substituted C1–C3 hydrocarbon radical, with a particular value for $R^2$ being C1–C24 alkyl, especially methyl; and wherein (x+y)/z is a number in the range of 0.5 and 4.0.

The siloxysilicate is selected on the basis of the properties desired. For example, volumizing effects without substantial stiffness or stickiness may be obtained with liquid MQ resins of Formula IB Formula IB

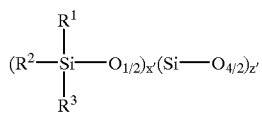

wherein x'/z' is a number between 0.5–1.5; x' and z' are selected so that the MQ resin has a viscosity in the range of $1.0 \times 10^3$–$1 \times 10^6$ centipoise (cps), particularly $1.5 \times 10^3$–$1 \times 10^6$ centipoise (cps); $R^1$ and $R^3$ are each independently selected from the same group as defined for $R^4$, $R^5$, $R^6$ and $R^7$ of Formula IA; $R^2$ is selected from the same group as described for $M^1$ and $M^2$. Such compositions are described in a copending case U.S.

Ser. No. 09/169,656 filed Oct. 9, 1998, and owned by the same company. A particular MQ useful as a volumizer is a liquid trimethylsiloxysilicate polymer, especially with an M:Q ratio of 1 (for example a resin obtained from General Electric Company, Waterford, N.Y. as "MQ-A") wherein (x+y)/z is a number in the range of 0.5 and 1.5, and is preferably equal to 1; and the values for $R^4$, $R^5$, $R^6$, $R^7$, x, y, z, $M^1$ and $M^2$ are selected to so that the MQ resin is a liquid having a viscosity of $1.0 \times 10^3 – 1 \times 10^6$ centipoise, for example, $1.5 \times 10^3 – 1 \times 10^6$ centipoise and particularly 1000–100,000 cps.

Other MQ resins include MQ-B (50% solution of solid trimethylsiloxysilicate in cyclomethicone); MQ-D (tetradecyldimethylsiloxysilicate); MQ-E (octadecyldimethylsiloxysilicate); MQ-F ((C20–24) alkyldimethyl-siloxyilicate); MG-G ((C16–C18) alkyldimethylsiloxysilicate); and MQ-H (poly(oxyethylene) dimethylsiloxysilicate); all from the General Electric Company, Waterford, N.Y. (with MQ's D, E, F, and G having each M unit of the polymer substituted with a long chain alkyl group; MQ-H having each M unit of the polymer substituted with a poly(oxyethylene) group of from 12 to 13 oxyethylene units per group; MQ-B being commercially available; and MQ's G and H being described in U.S. Pat. No. 5,684,112. Another example of a suitable MQ resin is a solid MQ Dow Corning 749 from Dow Corning Corporation, Midland, Mich.

Stabilizers include one or more members selected from the group consisting of:

(a) long chain fatty alcohols with greater than 14 carbons, for example C20–40, and mixtures of such long chain fatty alcohols (for example, a C>14 alcohol and ethene homopolymer PETROLITE C-7138 from Petrolite Corporation, St. Louis, Mo.).

(b) acrylates/steareth-20 methacrylate copolymer (for example, ACULYN® 22, from Rohm & Haas, Philadelphia, Pa.); and acrylates copolymer (for example, acrylates copolymer (ACULYN® 33); ACUSOL®-445, -810, and -830; ACRYSOL® ASE 75 from Rohm & Haas); and acrylates/C10–30 alkyl acrylate crosspolymer (PEMULEN™ polymeric emulsifiers from BF Goodrich Company, Brecksville, Ohio, particularly products designated as TR-1 and TR-2). For the acrylates copolymer (ACULYN® 33) product (having a pH in the range of 2.1–3.5), a neutralization step is performed with sodium phosphate (such as disodium phosphate), sodium hydroxide or a cosmetically acceptable organic amine to increase the pH to approximately 6.5.

(c) agents described in U.S. Pat. No. 5,015,415 (incorporated by reference herein) especially N,N-disubstituted phthalamic acids and their ammonium salts selected from the group consisting of Formula III:

Formula III

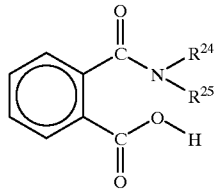

where $R^{24}$ and $R^{25}$ may be the same or different and are each selected from the group consisting of C10–C40 straight and branched chain alkyl groups, and C10–C40 straight and branched arylalkyl groups (for example, where $R^{24}$ and $R^{25}$ are the same and are each selected from the group consisting of stearyl and hydrogenated tallow such as STEPAN SAB-2 and STEPAN TAB®-2 from Stepan Company, Northfield, Ill.).

The stabilizing agents should be of a grade and purity acceptable for cosmetic use or purified as needed to be cosmetically acceptable. A further discussion of some of these agents may be found in U.S. Pat. No. 5,015,415 to Goze et al and in our copending patent application U.S. Ser. No. 08/933,521.

The aqueous carrier for the stabilized shampoo compositions of this invention is usually water.

It is critical to note that the stabilization of these shampoos is not straightforward and conventional agents used to stabilize so-called linear silicones do not necessarily work with the shampoo compositions containing the branched chain silicones as described here. For example, ethylene glycol distearate, a very popular stabilizer for dimethicone, does not work in this invention, while the TAB-2 material stabilizes the MQ resins described here but does not effectively stabilize dimethicone except at high levels of addition, such as 5%.

In addition to the ingredients required for compositions of this invention, other optional ingredients can also be included. These ingredients include additional silicone components such as at least one nonionic silicone material that can be a dispersed, insoluble, nonionic silicone hair conditioning agent, said silicone hair conditioning agent comprising a non-volatile, insoluble, nonionic silicone fluid component. These non-volatile silicone fluids may be either a polyalkyl siloxane, a polyaryl siloxane, a polyalkylaryl siloxane or a polyether siloxane copolymer. Mixtures of these fluids may also be used. The dispersed silicone particles should also be insoluble in the shampoo matrix. This is the meaning of "insoluble" as used herein. Examples of suitable fluids include polydimethyl siloxanes with viscosities of 5–600,000 centistokes at 25 degrees C. (for example, the Vicasil series of materials from General Electric Company and the Dow Corning 200 series from Dow Corning Corporation), especially those having a viscosity of 60,000 cps.

Optionally, if traditional linear silicones are used in a 2-in-1 conditioning shampoo, some amount of conventional stabilizing agents may also be included.

Other optional ingredients include:

(a) viscosity controlling agents to increase or decrease viscosity such as polyvinyl alcohol, ethyl alcohol, acrylic acid polymers, cellulosic ethers, diethanolamide of a long chain fatty acid (for example, PEG 3 lauramide), block polymers of ethylene oxide and propylene oxide, sodium chloride, sodium sulfate, water-soluble polymers (such as xanthan gum, hydroxyethyl cellulose, guar gum, and starch) particularly a thickening agent such as hydroxyethyl cellulose, hydroxypropyl cellulose, guar hydroxypropyl trimonium chloride, xanthan gum;

(b) lipid vehicle materials which are water-insoluble compounds possessing both hydrophobic and hydrophilic moieties including naturally or synthetically derived fatty alcohols, fatty alcohol ethoxylates, and fatty esters, particularly fatty alcohols from 12–22 carbons, more particularly 12–18 carbons, and, even more particularly, cetyl alcohol, stearyl alcohol and mixtures thereof;

(c) conditioning agents if the formulation is to be used as a conditioner where the conditioning agent is selected from quaternary ammonium compounds, particularly dicetyldimonium chloride, distearyl ammonium chloride and other cationic materials as listed above under cationic surfactants (particularly distearyldimonium chloride, dimethicone, Polyquaternium-10 and Polyquaternium-7;

(d) fragrances (perfumes) such as cosmetically acceptable fragrances used in hair care products;

(e) preservatives, for example, antimicrobial agents, particularly a combination of methylchloromethylisothiazolinone and methylisothiazolinone (sold under the tradename KATHON® CG by Rohm and Haas, Philadelphia, Pa.) but also including benzyl alcohol, ethyl paraben, propyl paraben and imidazolidinyl urea, 1,3-dimethylol-5,5-dimethyl hydantoin ("DMDM hydantoin"), formalin, 2-bromo-2-nitropropane-1,3-diol ("Bronopol"), and combinations of the foregoing. Particular examples may also include a potentiator such as ethylenediamine tetraacetic acid or the sodium salt form, (for example, Bronopol and EDTA (such as 0.04% Bronopol and 0.1% EDTA); formalin, DMDM hydantoin and EDTA (such as 0.1% formalin, 0.45% DMDM hydantoin, and 0.2% EDTA));

(f) dyes or coloring agents, pearlizers (such as ethylene glycol distearate, sodium octyl sulfate, titanium dioxide, or mica), and opacifying agents (such as glycol distearate, fatty ethoxylates, latex opacifiers, stearamide monoethanolamine (MEA) stearate, sodium cetyl stearate and lanolin derivatives) suitable for use in hair care products;

(g) pH adjusting agents such as citric acid, sodium carbonate, etc.;

(h) sequestering agents such as ethylene diamine tetraacetic acid, ethylene diamine tetraacetic acid and sodium salts of the foregoing.

Such additives may be included on an individual basis in appropriate amounts, for example in the range of about 0.01%–60%, preferably from abut 0.5%–40% by weight of the total weight of the composition.

Particular examples of formulations for shampoo compositions are as follows:

Formula A

8–20% anionic surfactant such as ammonium lauryl sulfate (for example, 16.80%) 0.1–1.0% of a foam stabilizer/conditioning agent such as Polyquaternium-10 (for example, 0.25%)

1.0–4.0% of a foam stabilizer/viscosity modifier such as cocodiethanolamide (for example, 2.00%)

0.1–6.0% MQ resin such as MQ-A (for example, 2.50%)

0.3–5.0% of a stabilizing agent such as 2.0% of SAB-2 or TAB-2; or 1.65% of ACULYN® 33 materials optionally an effective amount of a fragrance (for example, 0.75%) and an effective amount of a preservative (for example, 0.07%).

Formula B

Formula A with:

0.1–1.0% of an antistatic agent/conditioner such as distearyl diammonium chloride (for example, 0.25%)

0.1–3.0% of a non-volatile silicone fluid such as dimethicone (for example, 1.00%)

(optionally with an additional amount of a stabilizing agent suitable for dimethicone)

In general the compositions of the present invention may be made by conventional adding and mixing techniques. If an MQ resin is used, the MQ resin may be added in several ways. In shampoo formulations, the MQ resin can be added separately, either alone or mixed with cyclomethicone or dimethicone as in the following examples. Alternatively, the MQ resin can be added to the heated oil phase prior to any emulsion formation.

It should also be noted that while a variety of MQ resins may be used under the spirit and scope of the invention, the properties that the MQ resins impart to hair will vary. Some MQ's may give volumizing effects, some MQ's may give shine and conditioning improvements, etc.

While the compositions of this invention have been described in terms of "comprising" it is also intended that the compositions include narrower compositions in terms of "consisting of" and "consisting essentially of". Also, while the compositions of the invention have been described as "comprising" it is to be understood that the compositions also include those made by combining the ingredients listed in the composition.

EXAMPLES

The following Examples are included as being illustrative of the invention but should not construed as limitations thereon. Unless otherwise indicated, in the Examples as elsewhere in the application, all percents are in weight percents based on 100% active level for all ingredients and all chemical and scientific terms have their usual and customary meanings unless otherwise specified. All temperatures are in degrees C. These conventions are also used throughout the rest of the patent application.

Example 1

Stability Testing Procedure

Formula samples for stability testing are put into a 2 oz. glass jar. The jars are placed in a constant temperature oven which is set at 49 degrees C. (120 degrees F.) and are checked periodically for visible separation. Visible separation is defined as a distinct separation of phases in the emulsion. Formulations are considered stable if no separation occurs during a 4 week time period. Formulations are considered unstable if a 1 cm separation or greater occurs within 4 weeks of being put in the oven.

Examples 2–8

For Examples 2–8 shampoo compositions were made using the procedures described below and the amounts and types of ingredients listed in Table I (percents by weight based on the total weight of the composition). The preservative used for all the Examples was methylchloromethylisothiazolinone and methylisothiazolinone (KATHON CG).

Example 2

Acrylates Copolymer Formulations

In a suitable vessel all but 10% of the distilled water and the sodium phosphate were combined and mixed for 10 minutes. The ammonium lauryl sulfate was added to the vessel and mixed for 5 minutes. The resulting solution was heated to 90 degrees C. The remaining portion of distilled water and the Polyquaternium-10 were premixed for 1–2 minutes and added to the vessel. In a separate vessel the cocadiethanolamide, guar gum and distearyldimonium chloride were combined and heated to 90 degrees C. with occasional stirring. When both vessels reached 90 degrees C., they were combined and mixed for 10 minutes. The vessel then was allowed to cool to 60 degrees C. The silicone MQ resin was added to the vessel and mixed for 15 minutes. The vessel was then cooled to 55 degrees C. The acrylates copolymer ("ACULYN® 33") and fragrance were premixed and added to the emulsion with mixing. The vessel was then allowed to finish cooling. When the temperature of the mixture reached 38 degrees C., the preservative was added. The final formulation was cooled to room temperature. The compositions were evaluated for stability using the procedure of Example 1 and the results are in Table II.

Examples 3–5

Ethylene Glycol Distearate Formulations

The procedure described for Example 2 was repeated, with the exception that the ethylene glycol distearate was added to the vessel containing the cocadiethanolamide and the distearyldimonium chloride which was still heated to 90 degrees C. Additionally, there was no guar gum in the formulation. The fragrance was added by itself when the vessel was cooled to 55 degrees C. The compositions were evaluated for stability using the procedure of Example 1 and the results are in Table II.

Examples 6–7

Distearyl Phthalic Acid Amide Formulations

The procedure described for Example 2 was repeated, with the exception that the distearylphthalic acid amide (TAB-2) was premelted and added when the batch was cooled to 55 degrees C. The fragrance was also added at this time, but not premixed with the melted distearyl phthalic acid amide. The compositions were evaluated for stability using the procedure of Example 1 and the results are in Table II.

Example 8

C20–40 Alcohol Formulations

The procedure described for Example 2 was repeated, with the exception that the C20–40 alcohol ("C>14") was added to the vessel containing the cocadiethanolamide and the distearyldimonium chloride which was still heated to 90 degrees C. Additionally, there was no guar gum in the formulation. The fragrance was added by itself when the vessel was cooled to 55 degrees C. The compositions were evaluated for stability using the procedure of Example 1 and the results are in Table II.

TABLE I

| Ingredient | Ex. 2 | Ex. 3 | Ex. 4 | Ex. 5 | Ex. 6 | Ex. 7 | Ex. 8 |
|---|---|---|---|---|---|---|---|
| distilled water | q.s. | q.s. | q.s. | q.s. | q.s. | q.s. | q.s. |
| ammonium lauryl sulfate | 16.80 | 16.80 | 16.80 | 16.80 | 16.80 | 16.80 | 16.80 |
| sodium phosphate monobasic | 00.30 | 00.30 | 00.30 | 00.30 | 00.30 | 00.30 | 00.30 |
| Polyquaternium-10 | 00.25 | 00.25 | 00.25 | 00.25 | 00.25 | 00.25 | 00.25 |
| cocodiethanolamide | 02.00 | 02.00 | 02.00 | 02.00 | 02.00 | 02.00 | 02.00 |
| guar gum | 00.22 | 00.00 | 00.00 | 00.00 | 00.22 | 00.22 | 00.00 |
| distearyldimonium chloride | 00.25 | 00.25 | 00.25 | 00.25 | 00.25 | 00.25 | 00.25 |
| ethylene glycol distearate | 00.00 | 02.00 | 03.o0 | 03.00 | 00.00 | 00.00 | 00.00 |
| C20–C40 alcohols (PETROLITE) | 00.00 | 00.00 | 00.00 | 00.00 | 00.00 | 00.00 | 02.00 |

TABLE I-continued

| Ingredient | Ex. 2 | Ex. 3 | Ex. 4 | Ex. 5 | Ex. 6 | Ex. 7 | Ex. 8 |
|---|---|---|---|---|---|---|---|
| MQ resin (MQ-A) | 02.50 | 02.50 | 02.50 | 01.00 | 02.50 | 02.50 | 02.50 |
| distearyl phthalic acid amide | 00.00 | 00.00 | 00.00 | 00.00 | 02.00 | 02.00 | 00.00 |
| acrylates copolymer | 01.65 | 00.00 | 00.00 | 00.00 | 00.00 | 00.00 | 00.00 |
| fragrance | 00.75 | 00.75 | 00.75 | 00.75 | 00.75 | 00.75 | 00.75 |
| preservative | 00.07 | 00.07 | 00.07 | 00.07 | 00.07 | 00.07 | 00.07 |

Stability Evaluations

Stability evaluations were done for compositions made according to Examples 2–8. The data are recorded in Table II.

ESCA Evaluation

ESCA (electron spectroscopy for chemical analysis) is used to qualitatively and quantitatively determine the elemental composition of solid surfaces. ESCA was used to estimate the deposition of MQ resins on wool surfaces. Wool is similar chemically and morphologically to human hair and is often used as a substitute for human hair because of greater ease of measurement. As is known to those skilled in the art, ESCA uses the photoelectric effect to obtain information about the chemical composition of the solid surface. The sample surface is irradiated by x-ray photons which interact with atoms in the surface of the material. If the photons are of sufficient energy, electrons are emitted from the orbitals of the surface atoms. The kinetic energies of these emitted photoelectrons are then measured by an electron spectrometer. The relationship that describes this process is $$BE = \text{x-ray energy} - KE$$

where KE and BE are the measured kinetic energy and the calculated binding energy of the emitted photoelectron, respectively. The electron binding energy is characteristic of the element and electronic subshell from which it is emitted and serve to identify different elements on solid surfaces. The characteristic peak of the MQ resin was first determined using the pure substance. The areas of the peaks present on the test sample were used to determine the relative concentrations of the elements in the sample surface. For MQ resin deposition, the Si peak shows up in a distinct shape which allows for the calculation of the percent Si present. For each sample tested, 3 replicate wool swatches are prepared. Of the three swatches, 2 are analyzed initially. If there is a large variance in the 2 measurements, a third sample is run for verification. This process was run on Examples 2–8 and measurements taken at the times noted in Table II. The data are shown in Table II as atomic percent silicon.

TABLE II

| Example Number | Age of sample at time of treatment | ESCA | Stability |
|---|---|---|---|
| 2 | 6 days | 7.07 | stable |
| 2 | 16 days | 6.48 | stable |
| 2 | 50 days | 2.40 | stable |
| 3 | n/a | n/a | unstable |

TABLE II-continued

| Example Number | Age of sample at time of treatment | ESCA | Stability |
|---|---|---|---|
| 4 | n/a | n/a | unstable |
| 5 | n/a | n/a | unstable |
| 6 | 5 days | 9.21 | stable |
| 7 | 69 days | 9.19 | stable |
| 7 | 117 days | 9.29 | stable |
| 8 | 62 days | 4.67 | stable |

Examples 9–12

Examples 9–12 were made using the amounts of materials listed in Table III and also 0.75% fragrance and 0.07% methylchloromethylisothiazolinone and methylisothiazolinone (KATHON CG) (all percents are percents by weight based on the total composition). Stability was evaluated using the method described above and that evaluation is also contained in Table III. As can be seen from Table II and III, the ethylene glycol distearate material that is used as a stabilizer for dimethicone is not an effective stabilizer for MQ resins in the present formulations. On the other hand, while the TAB-2 material is a very effective stabilizer for MQ resin, it is substantially ineffective in stabilizing dimethicone in the present examples.

Examples 9–10

Distearyl Phthalic Acid Amide Formulations with Dimethicone

The procedure described in Examples 6–7 was followed, with the exception that the dimethicone was added with mixing following the addition of MQ resin at 60 degrees C.

Example 11

C20–40 Alcohol Formulations with Dimethicone

In a suitable vessel all but 10% of the distilled water and the sodium phosphate dibasic were combined and mixed for 10 minutes. The ammonium lauryl sulfate was added to the vessel and mixed or 5 minutes. The sodium cumenesulfonate was then added and allowed to mix until dissolved. Next, the cocamidopropyl betaine was then added, followed by the EDTA. The resulting solution was heated to 90 degrees C. The remaining portion of distilled water and the Polyquaternium-10 were premixed for 1–2 minutes and added to the vessel. In a separate vessel the PETROLITE C-7138 alcohol material (C>14) was added and heated to 90 degrees C. with occasional stirring. When both vessels reached 90 degrees C., they were combined and mixed for 10 minutes. The vessel then was allowed to cool to 60 degrees C. The silicone MQ resin was added to the vessel, followed by the dimethicone and mixed for 15 minutes. The vessel was then cooled to 55 degrees C. and the fragrance was added to the emulsion with mixing. The vessel was then allowed to finish cooling. When the temperature of the mixture reached 38 degrees C., the preservative was added. The final formulation was cooled to room temperature.

Example 12

Acrylates Copolymer Formulation with Dimethicone

The procedure in Example 11 was followed, with the exception that the dimethicone was added with mixing following the addition of MQ resin at 60 degrees C.

Table III

| Ingredient | Ex. 9 | Ex. 10 | Ex. 11 | Ex. 12 |
|---|---|---|---|---|
| ammonium lauryl sulfate | 16.8% | 16.8% | 8.26% | 16.8% |
| sodium phosphate monobasic | 0.3% | 0.3% | 0.00 | 0.3% |
| tetrasodium EDTA | 0.00 | 0.00 | 0.1% | 0.00 |
| cocamidopropyl betaine | 0.00 | 0.00 | 9.00% | 0.00 |
| sodium phosphate dibasic | 0.00 | 0.00 | 0.2% | 0.00 |
| sodium cumenesulfonate | 0.00 | 0.00 | 0.86% | 0.00 |
| Polyquaternium-10 | 0.25% | 0.25% | 0.55% | 0.25% |
| cocodiethanolamide | 2.0% | 2.0% | 0.0 | 2.0% |
| guar gum | 0.22% | 0.22% | 0.00 | 0.22% |
| distearyldimonium chloride | 0.25% | 0.25% | 0.00 | 0.25% |
| dimethicone | 0.50% | 1.00% | 1.00% | 1.00% |
| MQ Resin A ("MQ-A") | 1.00% | 1.00% | 1.00% | 2.50% |
| distearyl phthalic acid amide | 2.00% | 2.00% | 0.00 | 0.00 |
| C20–40 alcohol (PETROLITE C>14) | 0.00 | 0.00 | 2.00% | 0.00 |
| ACULYN 33 stabilizer | 0.00 | 0.00 | 0.00 | 1.65% |
| distilled water | q.s. | q.s. | q.s. | q.s. |
| stability | unstable | unstable | stable | stable |

Note that ethylene glycol distearate, a known stabilizer for dimethicone, does not work in this invention. The ACULYN® 33 acrylates copolymer and PETROLITE C-7138 ingredients are effective stabilizers for dimethicone as well as the MQ resins; however, deposition of the MQ resins from emulsions containing these stabilizers falls off with time. On the other hand, emulsions containing TAB-2 are stable and deposition of the MQ resin does not fall off with time. TAB-2 is a very desirable MQ stabilizer, however, it is not nearly as effective in stabilizing dimethicone as can be seen from the examples in Table III.

Examples 13–17

The procedure described above for Examples 9–12 was repeated using 16.80% ammonium lauryl sulfate; 0.30 % sodium phosphate monobasic; 0.25% Polyquternium-10; 2.00% cocodiethanolamide; 0.22% guar gum; 0.25% distearyldimonium chloride; 0.75% fragrance; 0.07% preservative (KATHON CG) for each of the Examples 13–17 in addition to the amounts of ingredients listed in Table V.

TABLE V

| Ingredient | Ex. 13 | Ex. 14 | Ex. 15 | Ex. 16 | Ex. 17 |
|---|---|---|---|---|---|
| MQ resin A | 0.50% | 1.00% | 0.00 | 0.00 | 0.00 |
| MQ resin B | 0.00 | 0.00 | 2.50% | 2.50% | 2.50% |
| Distearyl phthalic acid amide | 1.00% | 2.00% | 2.00% | 0.00 | 0.00 |
| Acrylates copolymer | 0.00 | 0.00 | 0.00 | 1.65% | 0.00 |
| C20–C40 alcohols (Petrolite) | 0.00 | 0.00 | 0.00 | 0.00 | 2.00% |
| Distilled water | q.s. | q.s. | q.s. | q.s. | q.s. |

Evaluations of the Examples were performed as described above and the resulting data is in Table VI. Each of Examples 13–17 was judged to be stable as evaluated by the Stability Testing Procedure described above.

TABLE VI

| Example Number | Age of sample at time of treatment (days) | ESCA Deposition (Atomic % Si) |
|---|---|---|
| 13 | 9 | 3.92 |
| 13 | 43 | 5.05 |
| 13 | 182 | 4.64 |
| 14 | 6 | 5.32 |
| 14 | 41 | 5.43 |
| 14 | 125 | 5.49 |
| 15 | 3 | 1.17 |
| 15 | 37 | 1.50 |
| 15 | 79 | 1.33 |
| 16 | 2 | 2.4 |
| 16 | 70 | 0.79 |
| 17 | 7 | 1.22 |
| 17 | 82 | 0.65 |

Example 18

Example 18 was made using 16.80% ammonium lauryl sulfate; 0.30% sodium phosphate monobasic; 0.25% Polyquaternium-10; 2.00% cocodiethanolamide; 0.22% guar gum; 0.25% distearyldimonium chloride; 0.75% MQ resin (MQ-A); 1.00% dimethicone; 0.50 distearyl phthalic acid amide; 0.90% ACULYN 22 acrylates; 0.84% ACULYN® 33 acrylates copolymer, 1.76% sodium cumene sulfonate; 0.75% fragrance; 0.07% preservative (KATHON CG); and the remainder (q.s.) distilled water sufficient to make 100%. In a suitable vessel all but 10% of the distilled water and the sodium phosphate were combined, mixed for 10 minutes and heated to 50 degrees C. The ACULYN® 22 acrylates, ACULYN® 33 acrylates copolymer, and the ammonium lauryl sulfate were added to the vessel and the pH was increased to 7.0 using 50% sodium hydroxide and then mixed for 10 minutes. The sodium cumene sulfonate was added and mixed until uniform. The pH was then decreased to 6.0–6.5 using 50% citric acid. The remaining portion of the distilled water and the Polyquaternium-10 were premixed for 1–2 minutes and added to the vessel. In a separate vessel the cocadiethanolamide, guar gum and distearyldimonium chloride were combined and heated to 50 degrees C. with mixing. This was added to the main vessel with mixing. In a separate contained the distearyl phthalic acid amide was melted at 45–50 degrees C. and then added to the vessel with mixing. The silicone MQ resin was added to the vessel and mixed for 15 minutes. The dimethicone was added to the vessel and mixed for 15 minutes. The vessel was then allowed to begin cooling. When the temperature of the mixture reached 40 degrees C., the fragrance was added. After continued cooling, the preservative was added below 38 degrees C. The final formulation was cooled to room temperature.

We claim:

1. A stabilized shampoo formulation comprising
   (a) 5–30% of a mixed anionic and amphoteric surfactant system where the ratio of anionic to amphoteric is from 60:40–40:60 and wherein:
      (1) the anionic surfactant is selected from the group consisting of:
         (i) alkyl and alkyl ether sulfates of formula $R^{20}OSO_3M$ and $R^{20}O(C_2H_4O)_wSO_3M$, wherein $R^{20}$ is alkyl or alkenyl of 10–20 carbon atoms, w is a number from 1 to 10, and M is a water-soluble cation selected from the group consisting of ammonium, sodium, potassium and triethanolamine;
         (ii) reaction products of fatty acids esterified with isethionic acid and neutralized with sodium hydroxide;
         (iii) succinamates; and
         (iv) olefin sulfonates having 12 to 24 carbon atoms; and
      (2) the amphoteric surfactant is selected from the group consisting of:
         (i) derivatives of aliphatic secondary and tertiary amines in which the aliphatic radical can be straight chain or branched and wherein one of the aliphatic substituents contains from 8 to 18 carbon atoms and one contains an anionic water solubilizing group;
         (ii) zwitterionic surfactants in which the aliphatic radicals can be straight chain or branched, and wherein one of the aliphatic substitutents contains from 8 to 18 carbon atoms and one contains an anionic water-solubilizing group selected from the group consisting of carboxy, sulfonate, sulfate, phosphate, and phosphonate;
         (iii) betaines;
   (b) from 0.1–15% of at least one siloxysilicate material wherein the siloxysilicate is represented by Formula IA:

Formula IA

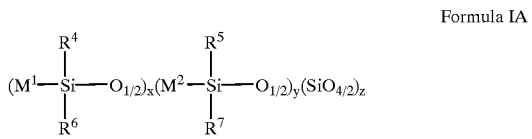

wherein
$R^4$, $R^5$, $R^6$, and $R^7$ are each independently selected from the group consisting of phenyl and C1–C12 branched and unbranched hydrocarbons;
$M^1$ and $M^2$ are each independently from the group consisting of
   (1) hydrogen;
   (2) phenyl;
   (3) phenethyl;
   (4) a polyether of Formula II:

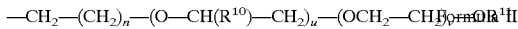

where n is a number from 1–20 and the —(CH$_2$)— chain may optionally contain 1 or 2 unsaturations; u and v are integers each independently selected from 0–20, provided that u+v>1; $R^{10}$ is selected from C1–C20 alkyl; and $R^{11}$ is selected from the group consisting of H, —CH$_3$ and —C(O)CH$_3$; and
   (5) C1–C24 branched and unbranched hydrocarbons optionally substituted by a halogen substituted C1–C3 hydrocarbon radical, with a particular value for $R^2$ being C1–C24 alkyl, especially methyl; and
wherein (x+y)/z is a number in the range of 0.5 and 4.0; or
wherein the siloxysilicate is represented by Formula IB:

Formula IB

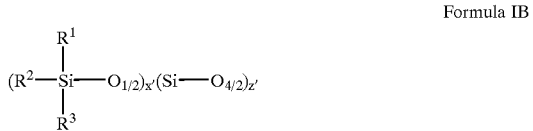

wherein x'/z' is a number between 0.5–1.5; x' and z' are selected so that the MQ resin has a viscosity in the range of $1.0 \times 10^3$–$1 \times 10^6$ centipoise; $R^1$ and $R^3$ are each independently selected from the same group as defined for $R^4$, $R^5$, $R^6$ and $R^7$ of Formula IA; $R^2$ is selected from the same group as described for $M^1$ and $M^2$;

(c) from 0.10–7.00% of at least one member of a selected stabilizing agent selected from the group consisting of
(i) long chain fatty alcohols with greater than 14 carbons;
(ii) acrylates/steareth-20 methacrylate copolymer; acrylates copolymer; and acrylates/C10–30 alkyl acrylate crosspolymer; and
(iii) N,N-disubstituted phthalamic acids and their ammonium salts selected from the group consisting of Formula III:

Formula III

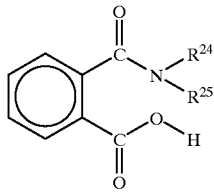

where $R^{24}$ and $R^{25}$ may be the same or different and are each selected from the group consisting of C10–C40 straight and branched chain alkyl groups, and C10–C40 straight and branched ary-lalkyl; and
(iv) mixtures of (i)–(iii); and
(d) an aqueous carrier;
wherein all percents are in weight percents based on 100% active level.

2. A stabilized shampoo formulation according to claim 1 comprising 0.1–10% of at least one siloxysilicate.

3. A stabilized shampoo formulation according to claim 1 comprising 0.1–7.0% of at least one siloxysilicate.

4. A stabilized shampoo formulation according to claim 1 comprising 0.10–5% of the stabilizing agent.

5. A stabilized shampoo formulation according to claim 1 comprising 0.10–3.0% of the stabilizing agent.

6. A stabilized shampoo formulation according to claim 1 comprising 1.5–3% of the stabilizing agent.

7. A shampoo formulation as claimed in claim 1 wherein $R^4$, $R^5$, $R^6$, and $R^7$ are each independently selected from the group consisting of C1–C12 branched and unbranched alkyl.

8. A shampoo formulation as claimed in claim 7 wherein $R^4$, $R^5$, $R^6$, and $R^7$ are each independently selected from the group consisting of branched and unbranched C1–C5 alkyl.

9. A shampoo formulation as claimed in claim 8 wherein $R^4$, $R^5$, $R^6$, and $R^7$ are each methyl.

10. A shampoo formulation as claimed in claim 1 wherein the siloxysilicate is represented by Formula IB:

Formula IB

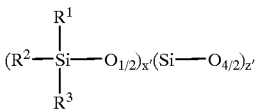

wherein x'/z' is a number between 0.5–1.5; x' and z' are selected so that the MQ resin has a viscosity in the range of $1.0 \times 10^3$–$1 \times 10^6$ centipoise; $R^1$ and $R^3$ are each independently selected from the same group as defined for $R^4$, $R^5$, $R^6$ and $R^7$ of Formula IA; $R^2$ is selected from the same group as described for $M^1$ and $M^2$.

11. A shampoo formulation as claimed in claim 8 wherein the MQ resin has a viscosity in the range of $1.5 \times 10^3$–$1 \times 10^6$ centipoise.

12. A shampoo formulation as claimed in claim 1 wherein (x+y)/z is a number in the range of 0.5–1.5 and the values for $R^4$, $R^5$, $R^6$, $R^7$, x, y, z, $M^1$ and $M^2$ are selected so that the siloxysilicate is a liquid having a viscosity of $1.0 \times 10^3$–$1 \times 10^6$ centipoise.

13. A shampoo formulation as claimed in claim 12 wherein the viscosity is $1.5 \times 10^3$–$1 \times 10^6$ centipoise.

14. A shampoo formulation as claimed in claim 13 wherein the viscosity is 1000–100,000 cps.

15. A shampoo formulation as claimed in claim 1 wherein the siloxysilicate is a member selected from the group consisting of:
(a) 50% solution of solid trimethylsiloxysilicate in cyclomethicone;
(b) tetradecyldimethylsiloxysilicate;
(c) octadecyldimethylsiloxysilicate;
(d) C20–24)alkyldimethyl-siloxyilicate;
(e) C16–C18)alkyldimethylsiloxysilicate; and
(f) poly(oxyethylene)dimethyl-siloxysilicate;
wherein for poly(oxyethylene)dimethyl-siloxysilicate each M unit of the polymer is substituted with a poly (oxyethylene) group of from 12 to 13 oxyethylene units per group, and wherein all substitutions are average values.

16. A shampoo formulation as claimed in claim 1 wherein (x+y)/z is 1.

17. A shampoo composition as claimed in claim 1 wherein the aqueous carrier is water.

18. A shampoo formulation as claimed in claim 1 additionally comprising silicone.

19. A shampoo formulation as claimed in claim 18 wherein the silicone is selected from the group consisting of non-volatile silicone fluids selected from the group consisting of polyalkyl siloxane, a polyaryl siloxane, a polyalkylaryl siloxane, a polyether siloxane copolymer and mixtures of the foregoing.

20. A shampoo formulation as claimed in claim 19 wherein the silicone comprises polydimethyl siloxanes with viscosities of 5–600,000 centistokes at 25 degrees C.

21. A shampoo formulation as claimed in claims 18 comprising a linear silicone.

22. A shampoo formulation as claimed in claim 1 optionally containing one or more of:
(a) a viscosity controlling agent selected from the group consisting of polyvinyl alcohol; ethyl alcohol; acrylic acid polymers; cellulosic ethers; diethanolamide of a long chain fatty acid; block polymers of ethylene oxide and propylene oxide; sodium chloride; sodium sulfate; xanthan gum; hydroxyethyl cellulose; hydroxypropyl cellulose; guar gum; starch; and guar hydroxypropyl trimonium chloride;
(b) lipid vehicle materials which are water-insoluble compounds possessing both hydrophobic and hydrophilic moieties selected from the group consisting of naturally or synthetically derived fatty alcohols, fatty alcohol ethoxylates, and fatty esters having from 12–22 carbons;
(c) conditioning agents selected from the group consisting of quaternary ammonium compounds;
(d) cosmetically acceptable fragrances;
(e) preservatives;
(f) cosmetically acceptable coloring agents selected from the group consisting of dyes, pearlizers, and opacifying agents;
(g) pH adjusting agents; and
(h) sequestering agents selected from the group consisting of ethylene diamine tetraacetic acid, and sodium salts of the foregoing.

* * * * *